United States Patent
Jain et al.

(12)

(10) Patent No.: US 10,421,695 B1
(45) Date of Patent: Sep. 24, 2019

(54) METAL-METAL BORIDE-METAL BASED CORE-SHELL PARTICLES AND A METHOD TO PRODUCE THE SAME

(71) Applicant: NEI Corporation, Somerset, NJ (US)

(72) Inventors: Mohit Jain, East Brunswick, NJ (US); Biju Mathew, Monroe, NJ (US)

(73) Assignee: NEI Corporation, Somerset, NJ (US)

( * ) Notice: Subject to any disclaimer, the term of this patent is extended or adjusted under 35 U.S.C. 154(b) by 583 days.

(21) Appl. No.: 14/803,673

(22) Filed: Jul. 20, 2015

Related U.S. Application Data (60) Provisional application No. 62/026,588, filed on Jul. 18, 2014.

(51) Int. Cl.
  *C06B 45/30* (2006.01)
  *C06B 27/00* (2006.01)
  *A61K 49/00* (2006.01)

(52) U.S. Cl.
  CPC .......... *C06B 45/30* (2013.01); *A61K 49/0004* (2013.01); *C06B 27/00* (2013.01)

(58) Field of Classification Search
  CPC ...... C06B 45/30; C06B 27/00; A61K 49/0004
  See application file for complete search history.

(56) References Cited

U.S. PATENT DOCUMENTS

| | | | |
|---|---|---|---|
| 9,421,732 B2 * | 8/2016 | Anderson | ................. B32B 5/16 |
| 2014/0225024 A1 * | 8/2014 | Kim | ...................... H01F 1/0306 |
| | | | 252/62.55 |

OTHER PUBLICATIONS

Gromov et al., Prop., Explos., Pyrotech. No. 5, 401-409 (2006).*
Saiyasombat et al., Nanotechnology 19 (2008) 085705 (7pp).*
Tartaj et al., J. Am. Chem. Soc. 2003, 125, 15754-15755 (Year: 2003).*
Il'in et al., Combustion, Explosion and Shock Waves, vol. 38, No. 1, pp. 123-126, 2002 (Year: 2002).*
Qi et al., Encyclopedia of Surface and Colloid Science, 2006, 6183-6207 (Year: 2006).*

* cited by examiner

*Primary Examiner* — Robert S Cabral
(74) *Attorney, Agent, or Firm* — William L. Botjer (57) ABSTRACT

A new class of energetic nanoparticles, and a method to produce the same. The energetic nanoparticles are differentiated from other metallic energetic nanoparticles by their core-shell nanostructure including an intermediate boride layer that provides oxidation protection and acts as an active mass. An intermetallic reaction occurs between aluminum and nickel. Aluminum based nanoparticles were used for the examples, but the principle is applicable to other materials as well.

12 Claims, 14 Drawing Sheets

METAL-METAL BORIDE-METAL BASED CORE-SHELL PARTICLES AND A METHOD TO PRODUCE THE SAME

CROSS REFERENCE TO RELATED APPLICATIONS

This application claims priority of U.S. provisional application No. 62/026,588 filed Jul. 18, 2015; the disclosure of which is hereby incorporated by reference.

STATEMENT OF GOVERNMENT SUPPORT OF INVENTION

This invention relates to the structure and method of Metal-Metal Boride-Metal core-shell particles. The work has been carried out under DoD Contract No.: FA8651-14-M-0044. The government has certain rights in the invention.

BACKGROUND

Core-shell nanoparticles with a metal core can be used in various applications, such as energetic, pyrotechnics, joining, medical imaging, liquid hydrocarbon fuels, munitions and energy storage. However, the presence of an oxide layer on the surface of the core metal nanoparticle can significantly reduce the performance of the core-shell nanoparticles. For example, intermetallic reactions in aluminum/nickel (Al/Ni) composites can have a dramatic increase in the rate, as well as velocity of reactions, when the particle size is reduced to a few nanometers in diameter. However, the presence of a passive $Al_2O_3$ layer on the surface of aluminum prior to coating with nickel will reduce the efficacy of Al/Ni core-shell structures for energetic applications. Calculations show that the presence of about 20 wt % oxygen in the powder reduces the amount of aluminum available for the energetic reaction to as little as 55 wt %, along with a reduction in the kinetics. It is not uncommon for aluminum powders to have 20 wt % oxygen. Consequently, the negative impact of an $Al_2O_3$ layer outweighs the benefits of high enthalpy nanoparticles.

Il'in et al. (IL'IN, A. P., GROMOV, A. A., TIKHONOV, D. V., YABLUNOVSKII, G. V., AND IL'IN, M. A., "Properties of Ultrafine Aluminum Powder Stabilized by Aluminum Diboride", Combustion, Explosion, and Shock Waves, 2002, v38, No. 1, p. 123-126) have demonstrated the feasibility of stabilizing ultrafine aluminum particles by forming $AlB_2$ on the surface immediately after synthesis of the particles. They synthesized $AlB_2$-coated ultrafine aluminum particles by the electric explosion of a boron coated aluminum conductor. The heat resistance of these particles increased by 30-40° C., compared to ultrafine aluminum particles coated with an oxide or hydroxide layer. Upon heating to 660° C., the degree of oxidation of $AlB_2$-coated aluminum particles was 6-16% lower than that of oxide/hydroxide coated aluminum particles. Further, the heat of combustion for $AlB_2$ coated particles was 2-4 kJ/g higher, compared to oxide/hydroxide coated particles. This may be due to the fact that $AlB_2$ also releases energy during combustion and act as an active energetic material, which can promote the vaporization of aluminum and increase the combustion temperature. There is no conversion of aluminum oxide to aluminum boride in the above described method.

$ALB_x$ Synthesis

According to the phase diagram of aluminum-boron, $AlB_{12}$ forms at 975° C., and it reacts with liquid aluminum to form $AlB_2$. Further, $AlB_{12}$ is a stable phase at room temperature if the boron content is >44.5 wt %. Conventionally, Al—B alloys are formed by the addition of $KBF_4$ in liquid aluminum, where liquid aluminum reduces boron halide to $AlB_2$ and $AlB_{12}$.

Kirillova et al (KIRILLOVA, N. V., KHARLAMOV, A. I., AND LOICHENKO, S. V., "Synthesis of a High-Boron Aluminum Boride via Borothermic Reduction of Alumina", Inorganic Materials, 2000, v36, No. 8, p. 776-782), have demonstrated the feasibility of synthesizing aluminum boride using alumina and boron as starting materials. According to Kirillova et al., the following reaction takes place when $Al_2O_3$ reacts with boron:

$$Al_2O_3+(x+2)B \rightarrow AlB_x+AlO\uparrow+2BO\uparrow$$

Initially, boron is oxidized by alumina to $B_2O_3$, followed by the formation and removal of a volatile metal oxide. Subsequently, the reaction intermediate $9Al_2O_3 \cdot 2B_2O_3$ is formed. Finally, $9Al_2O_3 \cdot 2B_2O_3$ is decomposed, and all the alumina reduced with boron is incorporated into the borides of various compositions.

Passivation Techniques for Aluminum Nanoparticles

Aluminum nanoparticles have been synthesized using a solution-assisted laser ablation technique, with oleic acid coating. The particles were minimally aggregated with an oxygen to aluminum ratio of 0.094 to 0.159. Aluminum nanoparticles coated with transition metal oxides are observed to have less aluminum oxide compared to uncoated particles. In the case of surface passivated pristine aluminum nanoparticles using perfluoroalkyl carboxylic acid self-assembled monolayers, the active aluminum content was found to be 15.4%, which is lower than the active aluminum content of conventional nanoscale aluminum particles. All of the above discussed methods do not provide a passivating layer that increases the combustion of aluminum nanoparticles.

Solvothermal Synthesis of Nanoscale Materials

In solvothermal synthesis, the chemical reaction takes place in a closed system in the presence of solvents (aqueous and non-aqueous), under pressure (usually between 1 atm and 10,000 atm), and at moderate temperatures (usually between 100° C. and 1000° C.). Solvothermal synthesis is used to synthesize nanoparticles of metals, metal-based compunds such as oxides, borides and carbides. Gu et-al (GU, Y., QIAN, Y., CHEN, L. AND ZHOU, F. "A mild solvothermal route to nanocrystalline titanium diboride", J. Alloys and Compounds, v352, 2003, v325-327) have synthesized nanocrystalline titanium diboride, using a solvothermal process. They started with amorphous boron powder, titanium tetrachloride ($TiCl_4$) and sodium. Sodium reduced $TiCl_4$ to titanium, which reacted with boron to form $TiB_2$. The presence of $TiB_2$ was confirmed using XRD and XPS. The particle size for as-synthesized $TiB_2$ was 15-40 nm.

SUMMARY OF THE INVENTION

The conventional energetic metallic nanoparticles have an oxide layer on the surface that reduces the energetic content of the particle as the oxide layer does not participate in the combustion, and acts as a passive material. The present invention is directed at synthesizing a new core-shell nanoparticle structure comprised of a metal core, a metal boride intermediate layer and an outer metal or metal oxide shell. The key characteristic of this core-shell structure is that it allows the use of both pristine metal, as well as oxygen containing metal particles, whereby the oxide surface layer of the metal particles is transformed into metal boride. Aluminum boride serves as an active constituent that also increases the energy content of the aluminum nanoparticles. Further, two synthesis methods were developed to synthesize these core-shell nanoparticles. An electroless plating/reverse micelle method was developed to coat the core with a metal layer, and a solvothermal synthesis method was developed to in-situ transform the metal oxide layer present on the surface of commercially available metal nanoparticles into an active metal boride layer. Results indicate that the surface of metal nanoparticle can be uniformly coated with metal nanocrystallites and metal boride. One specific example has been described in detail in the present application, wherein the core-shell nanoparticles are comprised of aluminum core-aluminum boride intermediate layer and nickel shell. An intermetallic reaction between Al and Ni was observed, demonstrating their energetic nature.

BRIEF DESCRIPTION OF THE DRAWINGS

For a better understanding of the invention, reference is made to the following drawings which are to be taken in conjunction with the detailed description to follow in which:

FIGS. 5(a) and 4(b) depict X-ray diffraction pattern of 5(a) as-received Al nanoparticles and 5(b) nickel coated Al nanoparticles

DESCRIPTION OF THE PREFERRED EMBODIMENTS

Figure 1:
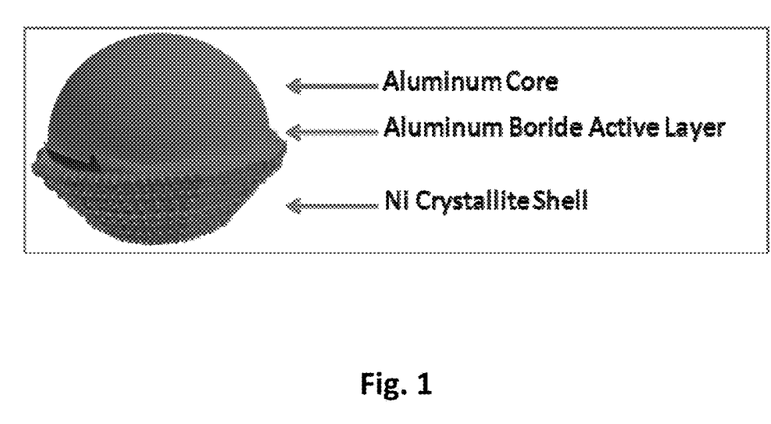
FIG. 1 is schematic representation of the metal-metal boride-metal core-shell nanoparticle

FIG. 1 shows a schematic of the metal-metal boride-metal core-shell nanoparticle structure of the present invention with an intermediate boride layer that provides oxidation protection and acts as an active mass. Those skilled in the art can also use the invention to form a metal oxide shell instead of a metallic shell. Example 1 discusses the method to form a uniform nickel coating on the surface of aluminum nanoparticles. Example 2 elaborates the method to form an aluminum boride coating on the surface of aluminum nanoparticles, using oxide layer present on the passivated aluminum nanoparticles as the aluminum source. Example 3 shows the synthesis method for aluminum-aluminum boride-nickel core-shell nanoparticle shown in FIG. 1. The average core diameter is in the range of 10 to 200 nm. The average shell thickness is in the range of 5 to 100 nm. The intermediate layer thickness is in the range of 5 to 50 nm.

Example 1: Procedure for Preparing Aluminum-Nickel Core-Shell Nanoparticles

Figure 2:
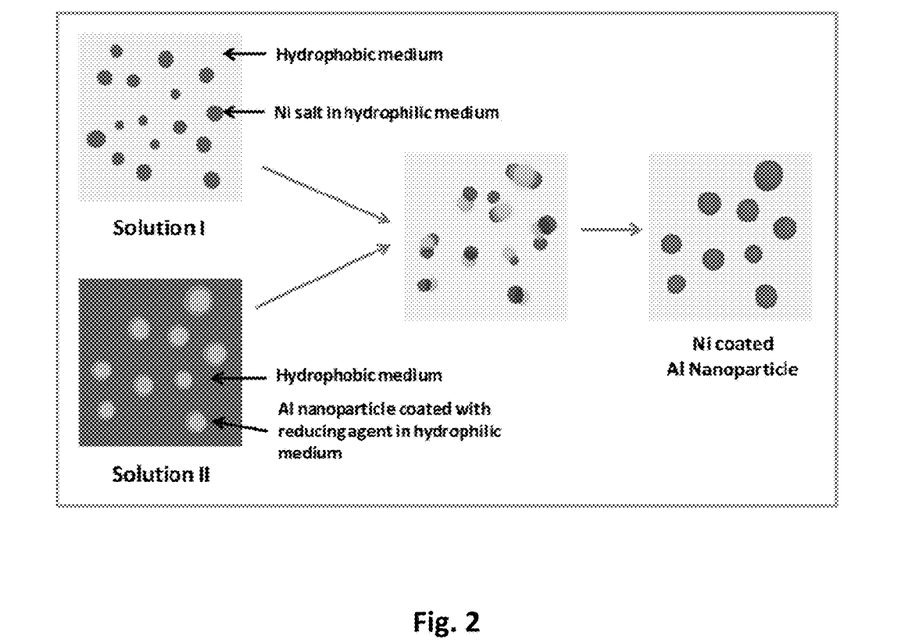
FIG. 2 is a schematic of the process to coat aluminum nanoparticles with nickel

In this invention we disclose a new solution based process, which is a combination of reverse micelle and electroless deposition methods. The chemical process essentially consists of using two separate solutions, one that contains $Ni^{2+}$ ions, and the other a reducing agent to convert $Ni^{2+}$ to $Ni^0$ (elemental nickel). FIG. 2 shows a schematic of the process. Solution 1 is a microemulsion, where the nickel salt is dissolved in a hydrophilic medium such as a water/hexanol mixture to form reverse micelles and it is subsequently dispersed in a hydrophobic medium such as cyclohexane. The hydrophobic medium can be an aromatic or an aliphatic molecule. Solution 2 is a microemulsion, where aluminum nanoparticles coated with a reducing agent such as sodium borohydride is dispersed in a hydrophilic medium such as a water/hexanol mixture to form a reverse micelles and it is subsequently dispersed in a hydrophobic medium such as cyclohexane. The reducing agent can be borohydride, hydrazine and a borane compound. When solution 1 and 2 are mixed, the reverse micelle containing the nickel salt combines with the reverse micelle containing aluminum nanoparticles and the reducing agent. This leads to a reaction between the reducing agent and the nickel salt to form a uniform nickel coating. The reaction is shown in equation 1.

$$2Ni^{2+}+NaBH_4+2H_2O \rightarrow 2Ni^0+NaBO_2+4H_2\uparrow \quad (1)$$

The major advantage of this method is that the reaction occurs only on the surface of aluminum nanoparticles, as the majority of sodium borohydride is present on the surface of these particles and not present separately in the solution. This not only allows for a uniform coating on the aluminum nanoparticles, but also reduces the probability of the formation of free standing nickel nanoparticles. Two types of aluminum particles having different particle sizes were used: Al-18 where the size varied between 10-50 nm, and Al-100 where the particle size was between 100-200 nm. The present invention applies to powders with particle size in the range of 10-200 nm.

In the nickel coating work, nickel nitrate was used as the nickel source. Initially, 2.5 g of nickel nitrate was dissolved in 10 mL of deoxygenated water in a 250 mL flask. Subsequently, 10 mL of hexanol was added to this solution, followed by the addition of 5.88 mL of Trinton X-100. The solution was then added to 100 mL of cyclohexane while stirring. The nickel nitrate concentration in this case corresponds to 0.07 M. The concentration of nickel salt can be varied from 0.05M to 0.25M. Subsequently, the mixture was ultrasonicated to form a microemulsion. In a separate flask, 0.32 g of sodium borohydride was dissolved in 10 mL deoxygenated water, followed by the addition of 10 mL of hexanol and 5.88 mL of Triton X-100. The mixture was added to 100 mL of cyclehexane, while stirring, followed by ultrasonication. The reducing agent concentration in this case corresponds to 0.07 M. The concentration of the reducing agent can be varied from 0.05M to 0.25M. The microemulsion containing nickel salt (solution 1) was added dropwise to the microemulsion containing aluminum nanoparticles, while stirring. The mixture was stirred for another 30 minutes after the addition of solution 1. Finally, the coated aluminum nanoparticles were filtered and washed with ethanol. The filtered aluminum nanoparticles were dried in vacuum. Some of the samples were heat treatment in hydrogen at 350° C. We have also synthesized nickel under the same experimental conditions but without the presence of aluminum nanoparticles to make sure that we were forming nickel.

Figure 3A:
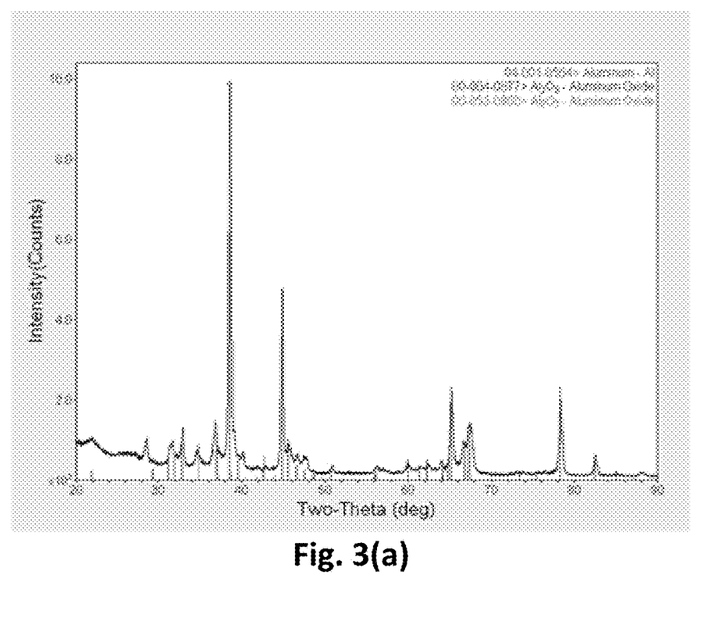
FIGS. 3(a) and 3(b) depict X-ray diffraction pattern of 3(a) as-received Al-18 nanoparticles; and 3(b) nickel coated Al-18 nanoparticles
Figure 3B:
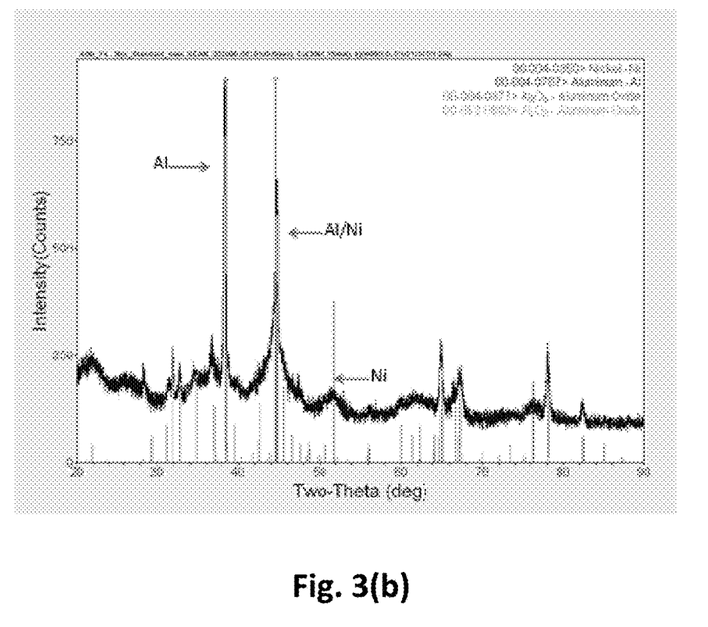
Figure 4A:
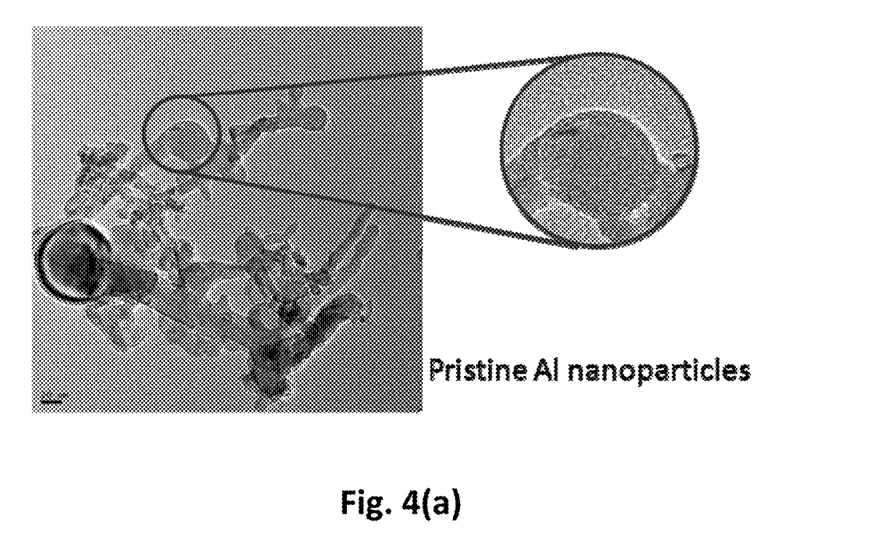
FIGS. 4(a) and 4(b) depict micrographs of 4(a) as-received Al nanoparticles (scale bar 20 nm); and 4(b) Al nanoparticles with Ni shell (scale bar 50 nm)
Figure 4B:
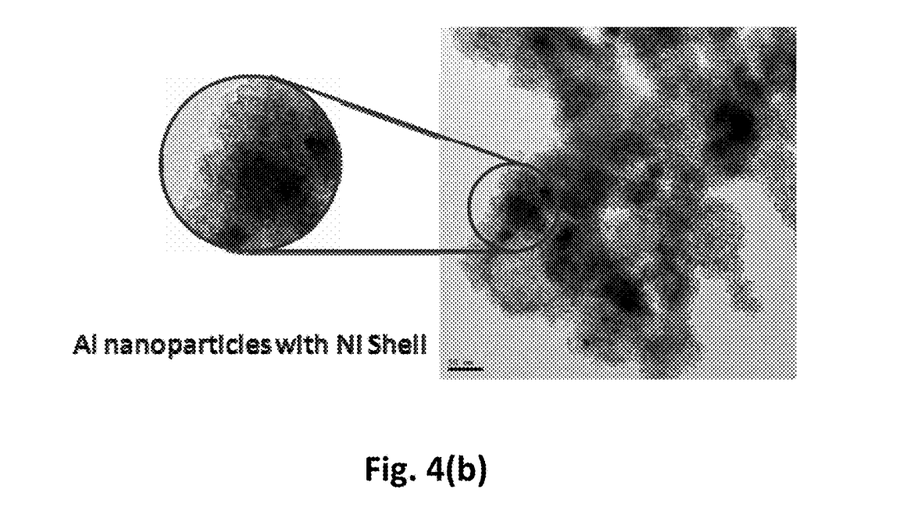

FIG. 3(a) shows the X-ray diffraction pattern of as-received Al-18 nanoparticles. Since these particles are much smaller in size compared to other commercially available Al nanoparticles, the alumina content is significantly higher, which is evident by the distinct $Al_2O_3$ peaks. FIG. 3(b) shows the X-ray diffraction pattern of Ni-coated aluminum nanoparticles after heat treatment at 350° C. (623 K). The broadening of the diffraction peak at ~44° confirms that both aluminum and nickel are present. FIG. 4(a) shows TEM micrographs of as-received Al-18 nanoparticles. The particle size is between 10 and 50 nm, with some of the particles having an elongated shape. The surface of the particles is smooth, as can be observed in the enlarged view. FIG. 4(b) shows Al-18 nanoparticles after Ni deposition using the electroless deposition/reverse micelle technique described above. It is evident that Ni has been homogeneously coated on the surface of Al nanoparticles. The average shell thickness is 20-40 nm, while the individual nickel particles are 5-10 nm in size. It should be noted that the shell thickness can be varied by altering the processing parameters. Accordingly, it is possible to vary the shell thickness from 5 nm to 100 nm. These core-shell aluminum-nickel particles, when evaluated for energetic performance, showed intermetallic reactions at ~650 and 800 K in an argon atmosphere.

The XRD, TEM and energetic data clearly demonstrates that Ni—Al core-shell nanoparticles can be synthesized with a thin nickel shell, and that the core-shell particles undergo intermetallic reaction at elevated temperatures.

Figure 5A:
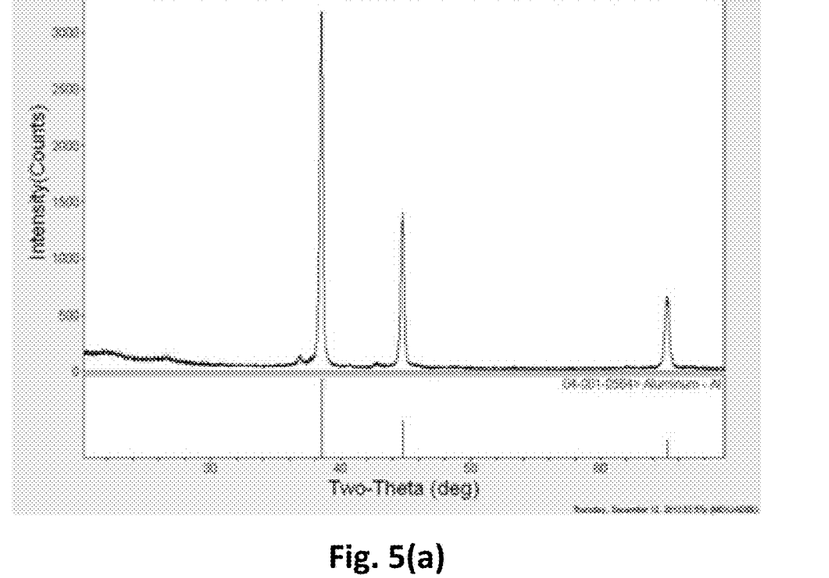
Figure 5B:
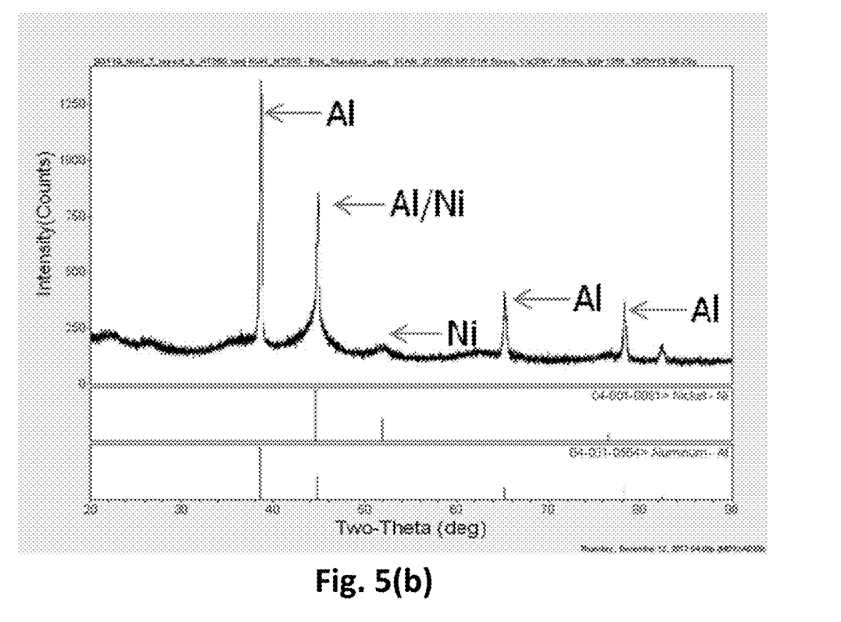

FIG. 5(a) shows the X-ray diffraction pattern of as-received Al-100 nanoparticles, which are phase pure. FIG. 5(b) shows the diffraction pattern of nickel coated aluminum nanoparticles. As discussed before, the broadening of the diffraction peak at ~44° confirms that both aluminum and nickel are present. The broadening also confirms that the crystallite size of nickel is in the nanoscale range.

Figure 6:
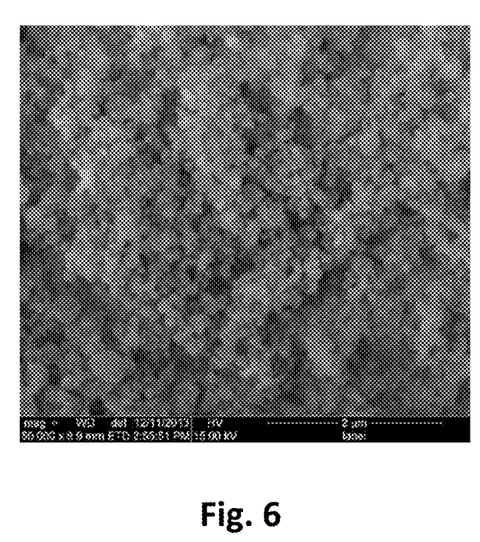
FIG. 6 depicts SEM micrographs of as-received Al-100 nanoparticles.
Figure 7:
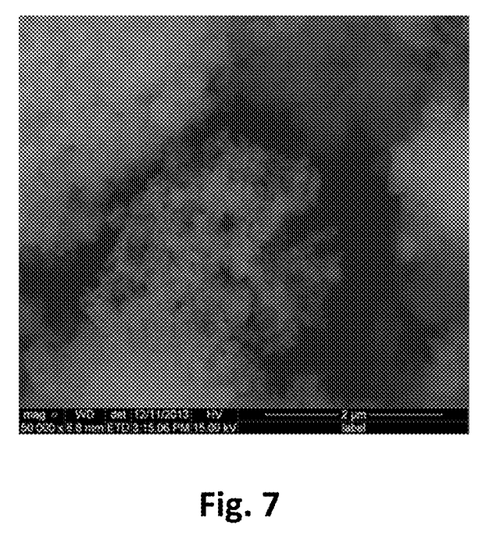
FIG. 7 depicts SEM micrographs of nickel coated Al-100 nanoparticles.

Both, as-received and nickel coated Al-100 nanoparticles were characterized for particle morphology using SEM. FIG. 6 shows the SEM micrographs of the as-received Al nanoparticles. The particles are in the range of 100-200 nm. FIG. 7 shows the SEM micrographs of nickel coated Al nanoparticles. The particle morphology is similar to that of uncoated Al nanoparticles, except that the interparticle space is reduced due to the formation of nickel on the Al nanoparticles. Additionally, the surface area of Al-100 nanoparticles increased from 19.5 $m^2/g$ for the as-received powder to 93 $m^2/g$ after coating with Ni. This gives a first order estimation of the size of the Ni nanoparticles on the surface of Al nanoparticles to be around 9.5 nm. This is consistent with the size of Ni nanoparticles observed in the TEM of Ni-coated Al-18 nanoparticles and further illustrates the versatility of the process to coat aluminum nanoparticles of various sizes and shapes.

Figure 8:
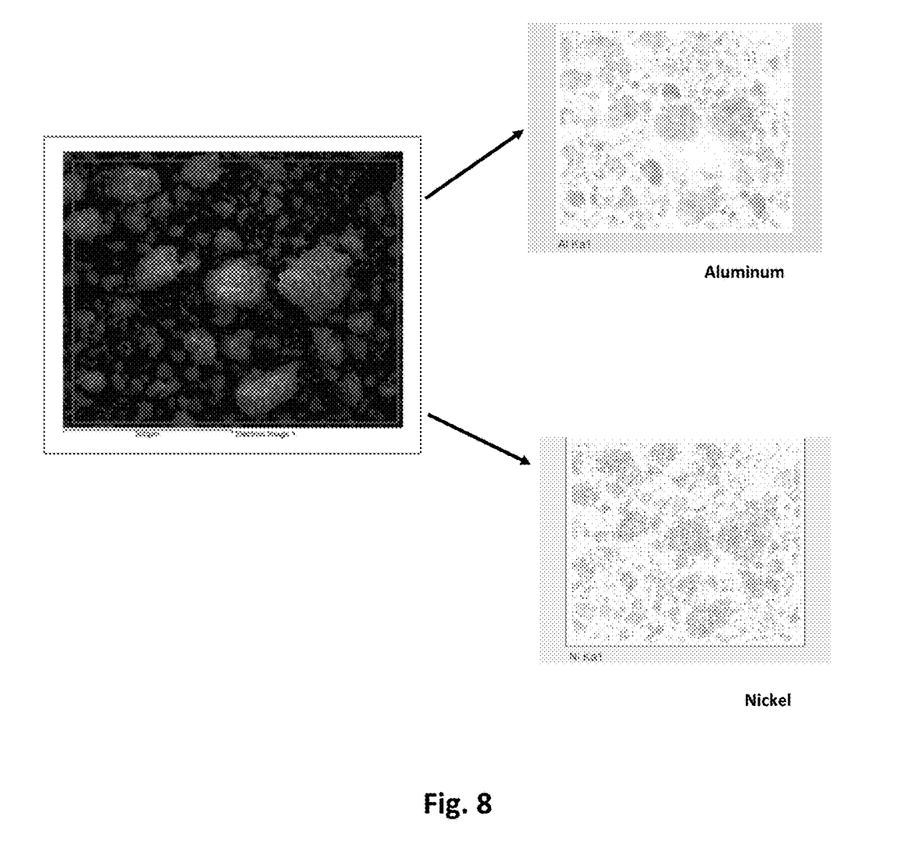
FIG. 8 depicts elemental mapping of Al and Ni on nickel coated Al-100 nanoparticles, using EDS

FIG. 8 shows the EDS map of nickel-coated Al nanoparticles, showing the distribution of Al and Ni. The co-existence of aluminum and nickel clearly demonstrates that Ni is uniformly coated on Al nanoparticles. The average Al to Ni ratio was 1.96:1, which was derived from an average of five different areas. Again, an exothermic intermetallic reaction between aluminum and nickel was observed, demonstrating their energetic properties. This is compared to physically mixed aluminum and nickel nanoparticles, where no intermetallic reaction was observed due to lack of intimate contact between nickel and aluminum.

Example 2: Procedure for Preparing Aluminum-Aluminum Boride Core-Shell Nanoparticles Conventional methods require high temperatures (>750° C.). However, this is not feasible for energetic applications as this will lead to the loss of the nanoparticle nature of aluminum due to the low melting point of aluminum (mp 660° C.). However, in a solvothermal synthesis method, high pressure and mild temperature (<250° C.) in a solvent can lead to reactions, which would otherwise require high temperatures.

The solvothermal reactor used for the experiments is able to withstand 30 MPa of pressure and 300° C. temperature. Initially, 2.3 g of $BI_3$ was dissolved in 125 mL of hexanol, followed by the addition of 0.4 g of aluminum nanoparticles, and 0.4 g of sodium metal (from 40 wt % sodium metal dispersion in kerosene). The mixture was stirred for 30 minutes and subsequently poured in to the reactor, under inert atmosphere. The reactor was heated to 215° C. and 12 MPa of pressure. A 12 MPa pressure caused the reaction to occur. A temperature range of 200-250° C. allowed this reaction to proceed. The pressure and temperature was maintained for 1 hour, followed by cooling to room temperature. The reaction mixture was filtered and washed with ethanol and dried in an oven in vacuum for 12 to 15 hours.

Figure 9A:
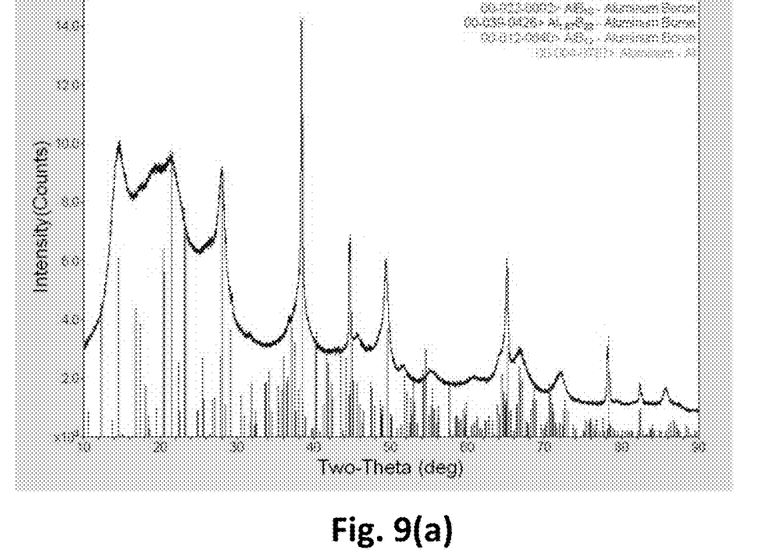
FIGS. 9(a) and 9(b) depict XRD pattern of 9(a) Al—AlBx nanocomposite particles and 9(b) aluminum nanoparticles (Al-100), before and after treatment in the reactor, without the addition of $BI_3$ and Na
Figure 9B:
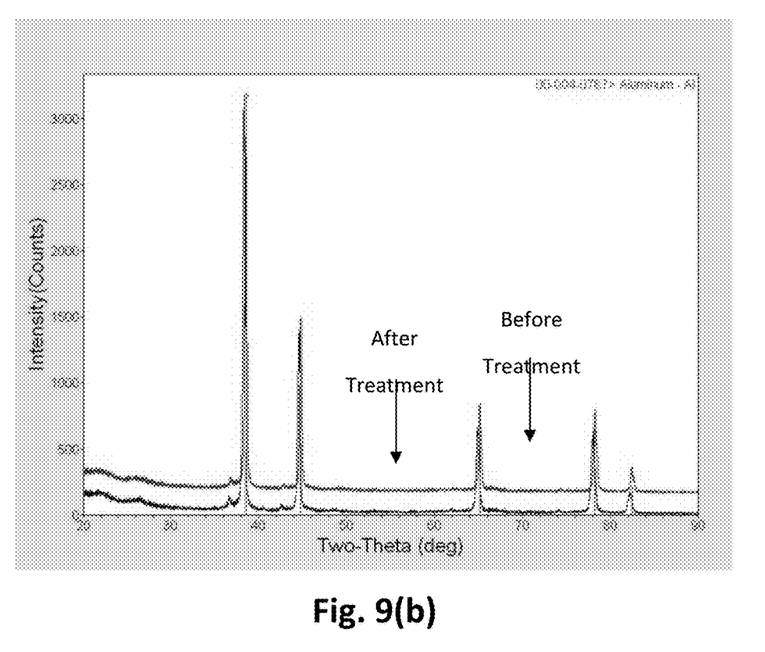

FIGS. 9(a, b) shows the XRD patterns of the as-synthesized Al—$AlB_x$ nanopowder, using Al-100 aluminum nanoparticles, as well as aluminum nanoparticles treated under similar conditions in the solvothermal reactor, but without boron iodide and sodium. Additional peaks, which can be observed when boron iodide and sodium are present in the reaction mixture, match with various phases of aluminum boride ($AlB_{10}$, $AlB_{12}$, $Al_{1.67}B_{22}$). The peaks corresponding to $AlB_x$ are broad as the $AlB_x$ is either not fully crystalline, or has a small crystallite size.

Figure 10:
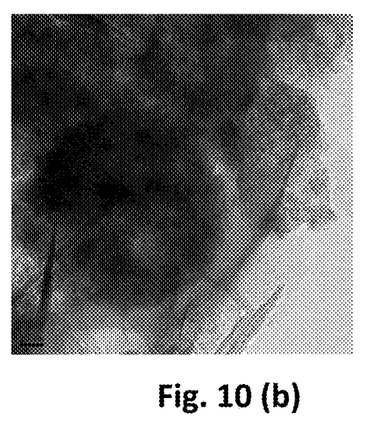
FIGS. 10(a) and 10(b) depict TEM micrographs of Al-100 aluminum nanoparticles of 10(a) as-received powder and 10(b) after conversion of the aluminum oxide to aluminum boride (scale bar is 20 nm).
Figure 10A:
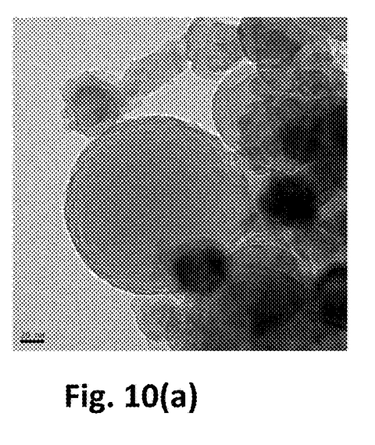

FIG. 10 (a) shows the TEM micrographs of as-received Al-100 aluminum nanoparticles, while FIG. 10(b) shows the same aluminum nanoparticles after solvothermal treatment with boron iodide and sodium. An amorphous layer, with a thickness of 10-20 nm can be seen on the surface of the nanoparticles. This layer can be attributed to various forms of aluminum boride observed in the X-ray diffraction pattern (FIG. 9). Based on the TEM and X-ray diffraction analysis, it can be concluded that commercially produced aluminum nanoparticles can be used to form Al—$AlB_x$ core-shell structures, where the aluminum oxide layer on the surface of passivated aluminum nanoparticles is used as the source of aluminum to form aluminum boride. Accordingly, a thin layer of aluminum oxide will lead to a thin layer of aluminum boride. Likewise, a thick layer of aluminum oxide will lead to a thick layer of aluminum boride. It is conceivable that the thickness of the aluminum boride layer can be varied between 5 nm and 50 nm, depending upon the thickness of the aluminum oxide and the size of the aluminum particles.

Figure 11:
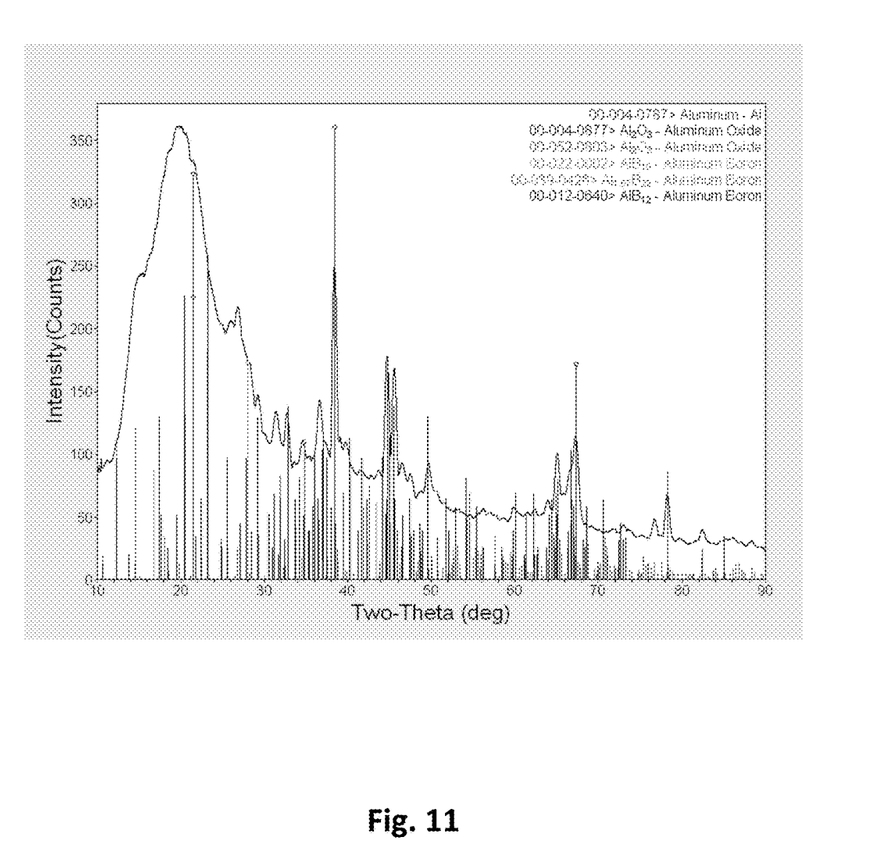
FIG. 11 depicts XRD pattern of AlBx-Al nanocomposite particles synthesized using solvothermal method, with Al-18 aluminum nanoparticles as the starting material.

Al-18 aluminum nanoparticles were also treated under similar processing conditions as Al-100 aluminum nanoparticles, in order to establish the versatility of the solvothermal processing technique. FIG. 11 shows the XRD pattern of as-synthesized powder after solvothermal treatment in the presence of $BI_3$ and Na. The intensity of the Al peak is significantly reduced. The most probable reason for this different behavior, compared to $AlB_x$ composite synthesized using Al-100 aluminum nanoparticles, is the size of the nanoparticles. Under the same synthesis conditions, since the thickness of the oxide layer is lower for the smaller particles (Al-18), compared to bigger particles (Al-100), the oxide layer on the smaller particles will be consumed faster during boride conversion reaction, leading to the exposure of Al core and its transformation to aluminum boride. This also indicates that the oxide layer is consumed first and converted to boride, prior to the conversion of aluminum metal to aluminum boride.

The energetic analysis on uncoated and $AlB_x$ coated Al-18 nm particles under oxy-argon flow demonstrated that the uncoated sample shows a large exothermic reaction at a temperature of 805 K (melting point of aluminum), due to increased oxidation rates with the formation of the liquid. A subsequent energetic analysis scan of the same sample after cooling to room temperature, showed no evidence of aluminum melting, meaning it was completely oxidized. The coated particles showed some evidence of oxidation around the melting point. It was noteworthy that the second run with the same sample still showed a slight endothermic reaction due to the melting of Al. This means that the $AlB_x$ layer acted as an oxidation barrier up to 1200 K (similar behavior was observed for Al-100 aluminum nanoparticles).

Based on the above discussion, it is seen that Al—$AlB_x$ nanocomposites can be synthesized using off-the-shelf passivated aluminum nanoparticles. Further, the $AlB_x$ formed on the surface participates during the exothermic combustion process, while the aluminum oxide layer is essentially inert material.

Figure 12:
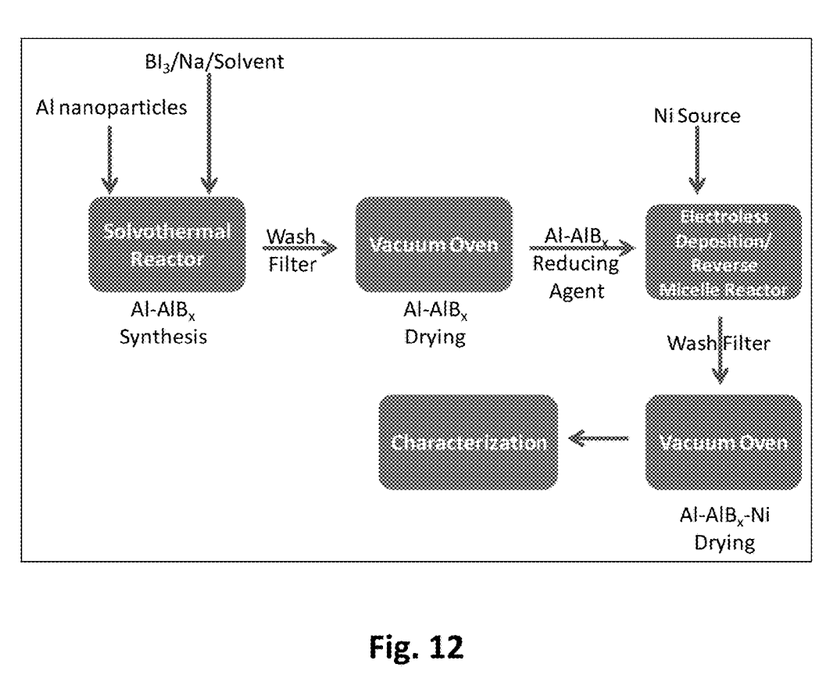
FIG. 12 depicts Schematic of the process used to synthesize aluminum-aluminum boride-nickel core-shell nanoparticles.

Example 3: Procedure for Preparing Aluminum-Aluminum Boride-Nickel Core-Shell Nanoparticles The aluminum-aluminum boride-nickel core-shell nanoparticles were synthesized by initially synthesizing aluminum-aluminum boride core-shell nanoparticles, using the method described in Example 2. Subsequently, the aluminum-aluminum boride core-shell nanoparticles were coated with nickel, using the method described in Example 1. FIG. 12 shows a schematic of the synthesis process used in this work. Initially, aluminum particles are mixed with sodium and boron iodide in solvent such as hexanol. The mixture is treated in the solvothermal reactor to in-situ form aluminum boride on the surface of aluminum particles. The treated powder is filtered and washed with alcohol and vacuum dried to remove the volatiles. Subsequently, the aluminum-aluminum boride powder is coated with nickel, using the process described in Example 1. The aluminum-aluminum boride powder is first dispersed in a mixture of hexanol and water that also contains the reducing agent such as sodium borohydride. The dispersion is added to a hydrophobic medium such as cyclohexane to form reverse micelles. A separate solution that contains the reverse micelles of nickel salt in hexanol and water mixture and dispersed in cyclohexane is prepared. The two solutions are combined to form a uniform coating of nickel on the surface of aluminum-aluminum boride nanoparticles due to the reaction between the reducing agent and the nickel salt. The nickel coated aluminum-aluminum boride particles are filtered and washed with alcohol followed by drying in the vacuum oven to remove organic volatiles.

Figure 13:
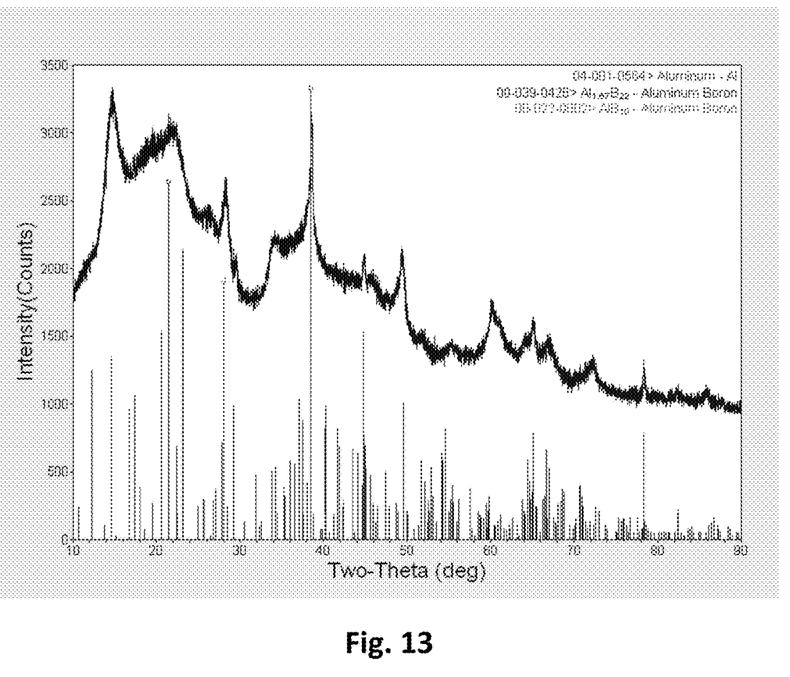
FIG. 13 depicts X-ray diffraction of as synthesized aluminum-aluminum boride-nickel core-shell nanoparticles (starting powder: Al-100).
Figure 14:
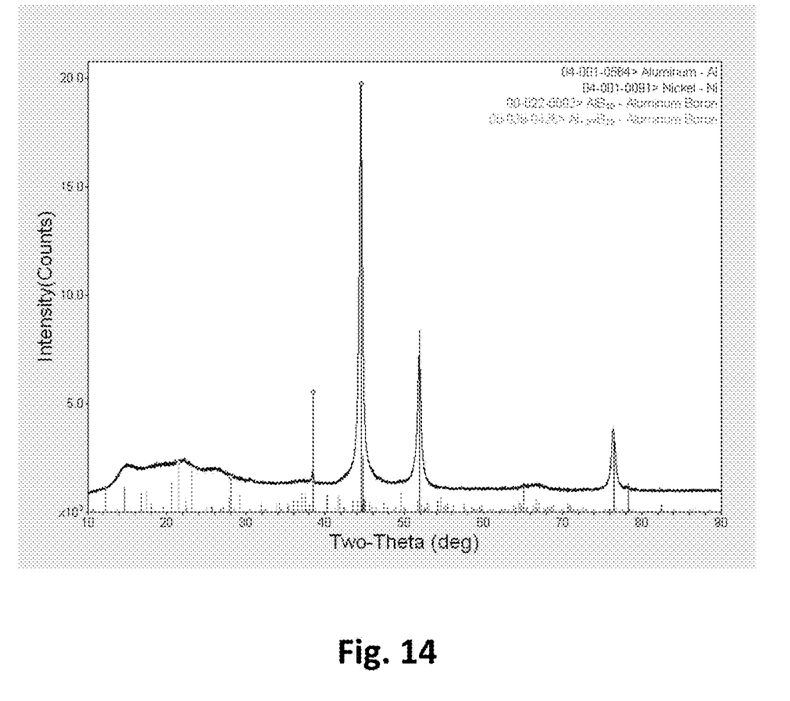
FIG. 14 depicts X-ray diffraction of as synthesized aluminum-aluminum boride-nickel core-shell nanoparticles, after heat-treatment (starting powder: Al-100)

FIG. 13 shows the X-ray diffraction pattern of as synthesized aluminum-aluminum boride-nickel core-shell nanoparticles synthesized using Al-100 nanoparticles. As observed before, Ni peaks are not present due to the amorphous nature of nickel coating. FIG. 14 shows the X-ray diffraction pattern, after heat treatment, showing the presence of metallic nickel.

Apart from the material system discussed above (aluminum core, nickel shell and aluminum boride intermediate layer), the core material can by any metal. The core material can also be any semi-metal such as boron, antimony, germanium, arsenic, and tellurium. The shell can be any metal or any metal oxide, and the intermediate layer can be any metallic boride.

The present invention has been described with respect to exemplary embodiments. However, as those skilled in the art will recognize, modification and variations in the specific details which have been described and illustrated may be resorted to without departing from the sprit and scope of the invention.

We claim:
1. A process of producing an energetic core-shell nanoparticle, comprising the steps of:
 a) supplying a metal or semi-metal nanoparticle core formed from a micro-emulsion solution comprising reverse micelles in a hydrophobic solvent containing the core particles and a reducing agent or a metal salt, the concentration of said reducing agent or metal salt being between 0.05 M and 0.25 M;
 b) forming a metal/semi-metal boride layer on the surface of the core particles; the metal/semi-metal boride layer being derived from a metal salt in a micro-emulsion; and
 c) depositing a metal/semi-metal shell on the boride layer.
2. The process as claimed in claim 1, wherein a pressure of 12 MPa was used to form the metal/semi-metal boride layer.
3. The process as claimed in claim 1, wherein a temperature of 200-250° C. was used to form the metal/semi-metal boride layer.
4. The process as claimed in claim 1 wherein the hydrophobic solvent is at least one of: an aliphatic and an aromatic molecule.
5. The process as claimed in claim 1 wherein the reducing agent is at least one of: a borohydride, hydrazine and a borane compound.
6. The process as claimed in claim 1 wherein the concentration of the metal salt in the formation of the metal/semi-metal boride layer is between 0.05-0.25 M.
7. A process of producing an energetic core-shell nanoparticle, comprising the steps of:
 a) supplying a metal or semi-metal nanoparticle core formed from a micro-emulsion solution comprising reverse micelles in a hydrophobic solvent containing the core particles and a reducing agent or a metal salt;
 b) forming a metal/semi-metal boride layer on the surface of the core particles; the metal/semi-metal boride layer being derived from a metal salt in a micro-emulsion;

wherein the concentration of the metal salt in the formation of the metal/semi-metal boride layer is between 0.05-0.25 M; and c) depositing a metal/semi-metal shell on the boride layer.

8. The process as claimed in claim 7, wherein a pressure of 12 MPa was used to form the metal/semi-metal boride layer.

9. The process as claimed in claim 7, wherein a temperature of 200-250° C. was used to form the metal/semi-metal boride layer.

10. The process as claimed in claim 7 wherein the hydrophobic solvent is at least one of: an aliphatic and an aromatic molecule.

11. The process as claimed in claim 7 wherein the reducing agent is at least one of: a borohydride, hydrazine and a borane compound.

12. The process as claimed in claim 7 wherein the concentration of said reducing agent is between 0.05 M and 0.25 M.

* * * * *